United States Patent [19]
Zimmer

[11] 3,934,589
[45] Jan. 27, 1976

[54] SURGICAL INSTRUMENT FOR STERILIZING WOMEN BY LIGATURE OF TUBES

[75] Inventor: Hildebrand Zimmer, Ahrensburg, Germany

[73] Assignee: Dragerwerk Aktiengesellschaft, Germany

[22] Filed: May 24, 1974

[21] Appl. No.: 473,220

[30] Foreign Application Priority Data
May 26, 1973  Germany............................ 2326988

[52] U.S. Cl................................ 128/303.1; 128/321
[51] Int. Cl.²..................... A61B 17/36; A61B 17/28
[58] Field of Search.................. 128/303.1, 321, 326

[56] References Cited
UNITED STATES PATENTS

| | | | |
|---|---|---|---|
| 463,785 | 11/1891 | Connable et al................. | 128/321 X |
| 702,472 | 6/1902 | Pignolet........................... | 128/303.1 |
| 2,831,174 | 4/1958 | Hilmo ........................... | 128/321 UX |
| 3,421,508 | 1/1969 | Nestrock.......................... | 128/303.1 |
| 3,674,031 | 7/1972 | Weiche............................. | 128/303.1 |

Primary Examiner—Channing L. Pace
Attorney, Agent, or Firm—McGlew and Tuttle

[57] ABSTRACT

A surgical instrument for sterilizing women by the ligation of the fallopian tubes comprises a probe having tongs with gripper means for engaging the tubes and means for directing a coolant to the vicinity of the gripper means for freezing of the tubes including a heater for subsequently heating the tubes. The probe advantageously includes a hollow central tube with a flared outer end at the probe tip and has an interior portion defining an evaporation chamber in which a coolant is evaporated to reduce the temperature at this end. A so-called Semm tongs extends through the tube and includes gripper elements at the flared end of the tube which may be moved outwardly to grip the fallopian tube of a woman to withdraw it into the flared end of the hollow tube where it may be frozen. The tip also includes a heater for reheating the frozen tubes. The opposite end of the probe includes a handle portion having a mechanical and electrical connection for the transmission of a coolant therethrough and the electrical current for actuating the heater.

6 Claims, 2 Drawing Figures

3,934,589

SURGICAL INSTRUMENT FOR STERILIZING WOMEN BY LIGATURE OF TUBES

BACKGROUND OF THE INVENTION

1. Field Of The Invention

This invention relates in general to the construction of surgical instruments and in particular to a new and useful surgical instrument which is provided with a tube through which tongs extend for grabbing the portion of a person's body and for withdrawing it into the flared end of the tube and which also includes means for cooling this end and for heating the end for selectively cooling and freezing parts of the body.

2. Description Of The Prior Art

At the present time instruments for the ligature of a woman's fallopian tubes in order to sterilize women are known.

Such an instrument is known under the designation Semm tongs. The ligature of tubes (thus the closure of the fallopian tubes) is effected so that upon the introduction of a trocar through the abdominal wall, the tubes are grasped by means of the introduced tongs consecutively at several locations and closed by electrocoagulation. At such an operation, there is a danger of secondary bleeding because, due to the necessary derivation of current during the electrocoagulation, the vessels located in the zone of treatment may become fragile. Consequently, after such an operation, the patients must remain under intensive medical care.

As a rule, the ligature of tubes is carried out under sight, with the aid of an optical device which is also introduced by means of a trocar. However, during the passage of current, smoke and vapor is developed, considerably affecting the sight and thereby the grasping of the tube by means of the same tongs which may lead to unintentional contacts with the surrounding tissue.

SUMMARY OF THE INVENTION

The invention is directed to a surgical treatment for sterilizing women by ligature of tubes in which the above mentioned drawbacks, i.e. the danger of secondary bleeding and the sight hindrance, are avoided.

In accordance with the invention, this problem is solved by providing the surgical instrument with tongs and a probe which can be cooled to a low temperature and subsequently heated up to the body temperature. With the aid of an instrument designed in this manner the ligation of tubes is induced by the effect of low temperature on the fallopian tube, thus by necrotizing the tube. The danger of damaging the surrounding tissue by the electric current is thereby eliminated. Moreover, no smoke or vapor is developed during the treatment with low temperature so that the surgeon's sight is not hindered. Due to these advantages, the instrument is particularly suitable for large-scale sterilizations because in general, there is no need of medical care after the treatment.

Accordingly it is an object of the invention to provide a surgical instrument for sterilizing women by ligation of tubes which comprises a probe having tongs with gripper means for engaging the tubes and which also includes means for directing a coolant to the vicinity of the gripper means for freezing the tubes and which furthermore includes a heater for reheating the tubes up to body temperature.

A further object of the invention is to provide a surgical instrument or probe which includes an elongated tube having a hollow central tubular portion with an outwardly flared distal end with Semm tongs extending therethrough and terminating in grippers at the flared end which may engage the tube or other part of the body and pull it into the flared end and which also includes an evaporative tip in which coolant is evaporated for cooling the seized body part and which further includes means for subsequently heating this part.

A further object of the invention is to provide a surgical instrument which is simple in design, rugged in construction and economical to manufacture.

For an understanding of the principles of the invention, reference is made to the following description of a typical embodiment thereof as illustrated in the accompanying drawings.

GENERAL DESCRIPTION OF THE PREFERRED EMBODIMENT

Figure 1:
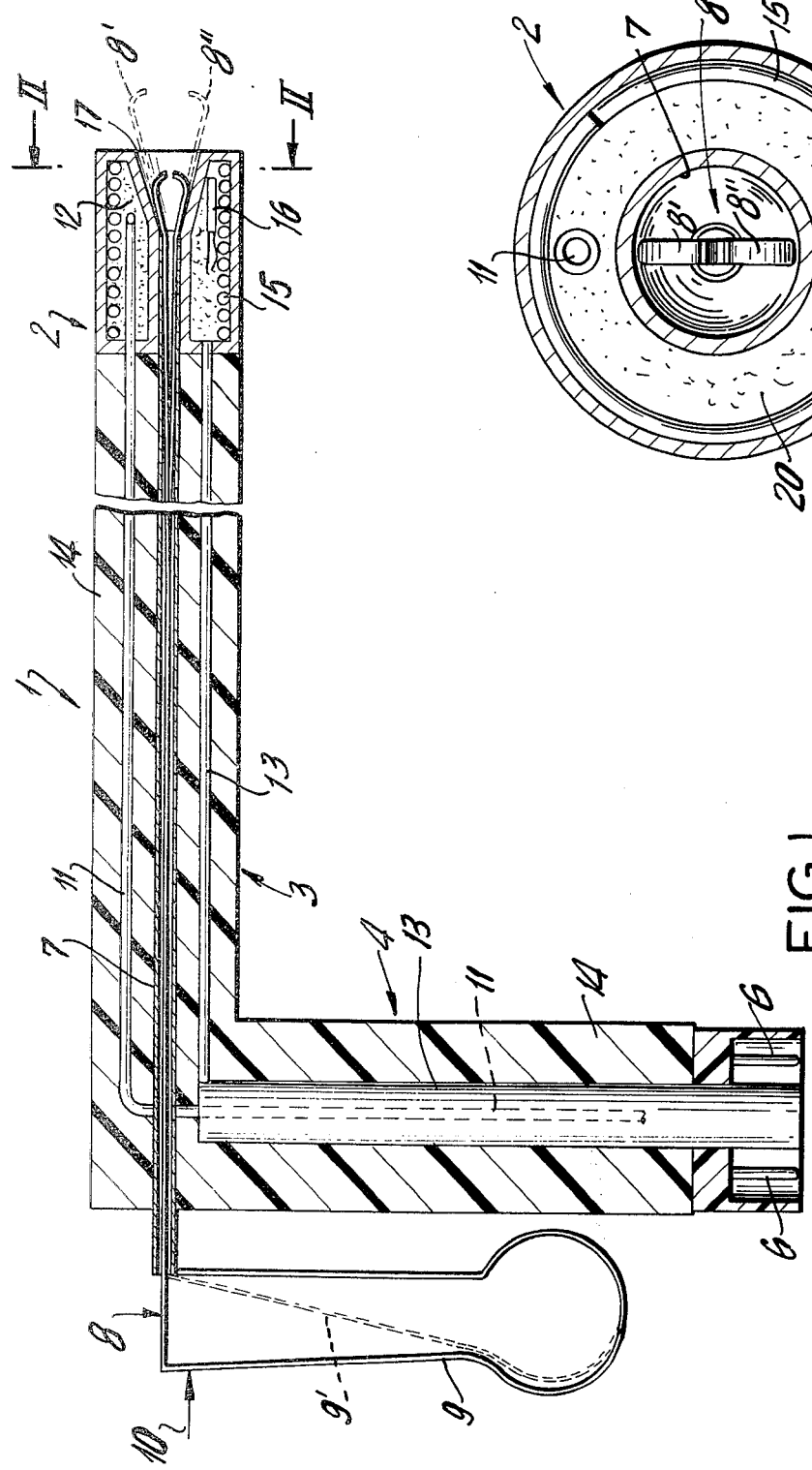
FIG. 1 is a longitudinal sectional view of an instrument constructed in accordance with the invention.

Referring to the drawings in particular the invention embodied therein comprises a surgical instrument or probe generally designated 1 which includes a probe tip 2 arranged at the end of a hollow tubular shaft portion 3 which is carried at the top of a handle 4. The free or lower end of the handle 4 is provided with mechanical fittings and electrical connections 6 for supplying the probe tip with electrical current and a cooling agent.

In accordance with the invention the probe shaft 3 includes a hollow central tube 7 having an outwardly flared end or trumpet shaped mouth 17. A so-called Semm tongs generally designated 8 includes rod-like elements which extend through the hollow tube 7 and terminate in hook shaped gripper ends 8' and 8''. The tongs 8 are biased by a spring ring 9 so that the grippers 8' and 8'' are withdrawn to the inner end of the flared portion 17 shown in FIG. 1. A pressure applied to the spring 9 in the direction of the arrow 10 will cause the spring to flex to the dotted line position 9' shown in FIG. 1 and cause the tong grippers 8' and 8'' to move into the dotted line position shown in the drawings.

A cooling agent is supplied through a supply line 11 which extends upwardly through the handle 4 and through the shaft 3 to an evaporation chamber 12 located in the probe tip 2. A return line 13 is defined in the shaft portion to extend from the probe tip backwardly to an annular conduit 13 which is defined around the conduit 11 in the handle 4. The return line is for evacuating the evaporated cooling agent. An insulation 14 preferably a vacuum insulation is advantageously included in both the shaft portion 3 and the handle portion 4.

Figure 2:
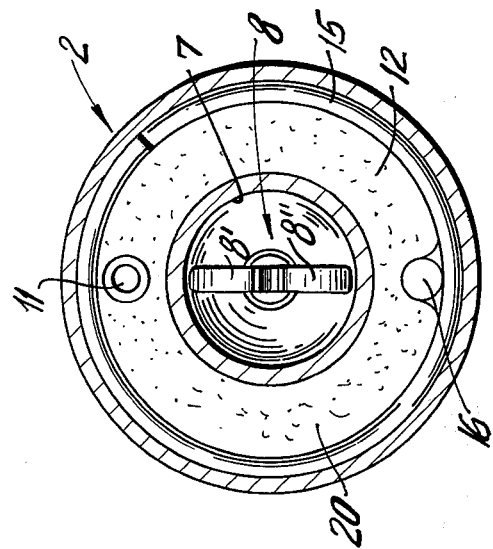
FIG. 2 is a section taken along the line II—II of FIG. 1.

The probe tip 2 which is also shown in FIG. 2 in a sectional view comprises an evaporation chamber 12 which has a circular cross section and preferably is filled with a silver wool 20 for improving the transmission of the cold. The supply line 11 for the liquid coolant leads into the evaporation chamber 12 and the evaporation chamber is connected to the return line 13 for the evaporated coolant. An electrical heater 15 is provided for reheating the probe tip 2 up to the body temperature after the fallopian tube or other body part is frozen. A temperature sensor 16 is provided for controlling the temperature of the probe tip 2. In the retracted position the grippers 8' and 8'' of the tongs 8 are surrounded by the evaporation chamber 12.

The ligature of the tubes is carried out by first gripping the fallopian tube by the grippers 8' and 8'' and at least partly drawing the tube into the front opening of the probe tip 2. Thereupon the probe tip is cooled down and this results in the closure of the fallopian tube. The tongs are released after reheating of the probe tip by means of the heating device 15. The flared end 17 of the probe tip facilitates the retraction of the fallopian tube into the end of the tube so that it can be cooled to a very low temperature by the coolant in the evaporation chamber 12.

While a specific embodiment of the invention has been shown and described in detail to illustrate the application of the principles of the invention, it will be understood that the invention may be embodied otherwise without departing from such principles.

I claim:

1. A surgical instrument for sterilizing women by necrosis of tubes, comprising a tubular probe having a bore therethrough and an enlarged cavity at a distal end thereof, tongs extending through the bore with a gripper jaw extending out the distal end of the cavity for engaging the tubes and being retractable into the enlarged end of the bore after it is engaged with the tubes, said tongs having an operating handle exteriorly of the probe for shifting the tongs in the bore and for operating the jaws of said tongs, means for directing a coolant to said probe around said gripper jaw when it is retracted into the cavity for freezing the tubes, and heater means in the vicinity of said gripper jaw when it is retracted for heating said tubes.

2. A surgical instrument according to claim 1, wherein said probe includes a shaft portion having a freezable probe tip, and including a central hollow tube, said tongs comprising a Semm tongs having a rod portion extending through said central tube and having said gripper jaw located at the distal end thereof, the gripper jaw having two opposed jaw portions, said bore being beveled outwardly at said distal end so that said gripper jaw portions may be retracted within the bore for holding the tubes therein.

3. A surgical instrument for freezing body parts, for example to sterilize women, comprising a shaft portion having a bore with a proximal end and an opposite distal end with walls adjacent said opposite distal end which flare outwardly, an annular coolant chamber formed in said shaft portion adjacent the opposite distal end, conduit means extending through said shaft portion for conducting a coolant to and returning a coolant from said coolant chamber for freezing said outwardly flaring end and hence any body part in the vicinity thereof, tongs having a handle portion at one end with a rod portion extending from said handle portion through said bore and terminating in a pair of opposed gripper jaws adjacent the outwardly flaring distal end, said gripper jaws being engageable around a part of the body and being movable into the bore through the flaring end, said jaws being contractible by the flaring walls of the bore when said tongs are withdrawn by engagement and movement of said handle portion.

4. A surgical instrument according to claim 3, wherein said tongs comprise a Semm tongs having said rod portion extending through said bore and said handle portion comprising a loop forming a spring end for advancing said rod portion with said gripper jaws outwardly from and inwardly of said outwardly flared end for engaging the part of the body and withdrawing it into the flared end.

5. A surgical instrument according to claim 3, including means in said probe distal end for heating the end.

6. A surgical instrument according to claim 4, wherein said probe includes a probe handle portion extending at an angle to said shaft portion, said handle portion having an electrical connection and a connection for connecting coolant to said probe tip, heater means in said probe tip connected to said electrical connection.

* * * * *